United States Patent [19]

Suiko

[11] Patent Number: 5,716,836
[45] Date of Patent: Feb. 10, 1998

[54] ANTI-SULFATED TYROSINE ANTIBODY SPECIFIC FOR SULFATED TYROSINE, PROCESS FOR PRODUCING THE SAME, AND HYBRIDOMA CAPABLE OF PRODUCING ANTI-SULFATED TYROSINE MONOCLONAL ANTIBODY SPECIFIC FOR SULFATED TYROSINE

[75] Inventor: Masahito Suiko, Miyazaki, Japan

[73] Assignee: Unitika Ltd., Hyogo, Japan

[21] Appl. No.: 340,427

[22] Filed: Nov. 14, 1994

Related U.S. Application Data

[63] Continuation of Ser. No. 24,298, Mar. 1, 1993, abandoned.

[30] Foreign Application Priority Data

Feb. 28, 1992 [JP] Japan ................................. 4-078986

[51] Int. Cl.$^6$ .......................... C12N 5/12; C07K 16/00; C07K 16/44
[52] U.S. Cl. ..................... 435/240.27; 530/387.1; 530/387.9; 530/388.1; 530/388.9
[58] Field of Search .................. 530/387.1, 387.9, 530/388.1, 388.9; 435/240.27, 240.2

[56] References Cited

U.S. PATENT DOCUMENTS

| | | | |
|---|---|---|---|
| 4,474,893 | 10/1984 | Reading ................................ | 436/547 |
| 4,546,161 | 10/1985 | Harvey et al. ........................ | 527/312 |
| 4,722,899 | 2/1988 | Hamaoka et al. ..................... | 435/172.2 |
| 4,777,127 | 10/1988 | Suni et al. ............................ | 435/5 |

OTHER PUBLICATIONS

Precup et al., FASEB J., 1991, 5(4):A522.
Jansen et al., Life Sciences, 1983, 33:2197.
Jansen et al., Biochim. Biophys. Acta, 1983, 131:305.
Omary et al., Molecular Immunology, vol. 29, No. 1, pp. 9–19 (Jan. 1992).
Liu et al., Archives of Biochemistry and Biophysics, vol. 255, No. 1, pp. 162–167 (1987).
Terranova et al., Science, vol. 226, pp. 982–985 (1984).
Goodman, Basic & Clinical Immunology, Fudenberg et al. (Ed.) Lange Medical Publications, Los Altos, pp. 32–40 (1976).
Galfre et al., Methods in Enzymology, vol. 73, pp. 3–47 (1981).
Campbell, Monoclonal Antibody Technology, vol. 13, Burdlon et al. (Ed.) Elsevier, New York pp. 158–203 (1984).
Goding, Journal of Immunological Methods, vol. 39, pp. 285–308 (1980).
Cot et al., Hybridoma, vol. 6, No. 1, pp. 87–95 (1987).

*Primary Examiner*—Frank C. Eisenschenk
*Attorney, Agent, or Firm*—Sughrue, Mion, Zinn, Macpeak & Seas

[57] ABSTRACT

An anti-sulfated tyrosine antibody specific for sulfated tyrosine which is capable of binding to sulfated tyrosine in the free state or present in a peptide chain, but not to unsulfated tyrosine. The anti-sulfated tyrosine antibody specific for sulfated tyrosine according to the invention can be used to assay sulfated tyrosine simply within a short period of time. A process for the production of the inventive antibody, as well as a hybridoma which is capable of producing anti-sulfated tyrosine monoclonal antibody specific for sulfated tyrosine is also provided.

2 Claims, 1 Drawing Sheet

ANTI-SULFATED TYROSINE ANTIBODY SPECIFIC FOR SULFATED TYROSINE, PROCESS FOR PRODUCING THE SAME, AND HYBRIDOMA CAPABLE OF PRODUCING ANTI-SULFATED TYROSINE MONOCLONAL ANTIBODY SPECIFIC FOR SULFATED TYROSINE

This is a Continuation of application Ser. No. 08/024,298 filed Mar. 1, 1993, now abandoned.

FIELD OF THE INVENTION

This invention relates to anti-sulfated tyrosine antibodies specific for sulfated tyrosine which are useful for the immunological measurement of sulfated tyrosine, to a process for the production of the antibody and to a hybridoma capable of producing anti-sulfated tyrosine monoclonal antibodies specific for sulfated tyrosine.

BACKGROUND OF THE INVENTION

A number of proteins in the living body are modified after their translation by sulfate transferase in the presence of 3'-phosphoadenosine 5'-phosphosulfate (hereinafter referred to as "PAPS") as a sulfate group donor in the following manner.

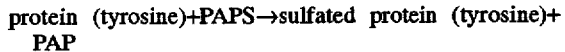

protein (tyrosine)+PAPS→sulfated protein (tyrosine)+ PAP (PAP: 3'-phosphoadenosine 5'-phosphate)

This sulfation reaction is specific for tyrosine residues of protein molecules and its influences on a number of protein species, such as regulation of their physiological activities, diversification of their functions and alteration of their stability against decomposition have been reported.

For example, it has been reported that sulfated fibronectin inhibited metastasis of mouse melanoma (*Science*, vol. 226, p. 982, 1984). In addition to this, it is considered that sulfated tyrosine residues are present in a variety of proteins to perform regulation of various physiological activities, examples of such proteins including complement, alpha-fetoprotein, entactin, thyroglobulin, collagen V, alpha-2-antiplasmin, hirudine, leucine enkephalin, gastrin and the like.

Also, attention has been directed at PAPS as a sulfate group donor to tyrosine and to its application as to pharmaceutical drugs. For example, Liu et al. (*Proc. Natl. Acad. Sci. USA*, vol. 81, p. 3695, 1984) have measured the amount of sulfated tyrosine in cancer cell protein and reported that the sulfated tyrosine content was quite low in comparison with the amount present in normal cells, and Suiko et al. (*Biochem. J.*, vol. 247, p. 210, 1987) have found that such a sharp decrease is due to the inhibition of PAPS formation in cancer cells.

In order to accelerate research and development on PAPS and sulfated tyrosine and apply them as to pharmaceutical drugs, it is necessary to be able to measure sulfated tyrosine and tyrosine residues accurately and simply.

Such a measurement has been made by the use of a radioactive isotope or high performance liquid chromatography (hereinafter referred to as "HPLC"). In the former radioisotope-aided process, [$^{35}$S] sulfated tyrosine is incorporated into cells, protein molecules containing [$^{35}$S] sulfate groups are hydrolyzed and the hydrolyzed protein fragments are isolated by thin layer chromatography or the like and radioactivity detected. In the latter HPLC-aided process, protein in a sample is hydrolyzed and analyzed using an HPLC column.

In these prior art processes, however, it is necessary to employ a hydrolysis step which requires complex handling and is time-consuming. In addition, the radioisotope-aided process is useful only within a limited application range, and the HPLC-aided process is not suitable for measurement of microquantities because of its poor sensitivity.

SUMMARY OF THE INVENTION

Accordingly, an object of the present invention is to provide anti-sulfated tyrosine antibodies specific for sulfated tyrosine for use in a simple and rapid assay of sulfated tyrosine, as well as a process for the production of antibody and a hybridoma which is capable of producing an anti-sulfated tyrosine monoclonal antibody specific for sulfated tyrosine.

With the aim of overcoming the above-described problems involved in the prior art, intensive studies have been conducted and anti-sulfated tyrosine antibodies specific for sulfated tyrosine have been found which rendered possible an immunoassay of sulfated tyrosine. The present invention has been accomplished on the basis of this finding.

The anti-sulfated tyrosine antibody specific for sulfated tyrosine according to the present invention is an antibody which binds to sulfated tyrosine, but not to unsulfated tyrosine, and an anti-sulfated tyrosine monoclonal antibody specific for sulfated tyrosine according to the present invention is a monoclonal antibody which binds to sulfated tyrosine, but not to unsulfated tyrosine.

Accordingly, a first embodiment of the present invention provides an anti-sulfated tyrosine antibody specific for sulfated tyrosine which is capable of binding to sulfated tyrosine as a free molecule or present as a residue in a peptide chain, but not to unsulfated tyrosine as a free molecule or present as a residue in a peptide chain.

A second embodiment of the present invention provides a process for the production of the above-described anti-sulfated tyrosine antibody specific for sulfated tyrosine which comprises immunizing a mammal against sulfated tyrosine or a protein complex thereof to obtain serum, and subsequently subjecting the serum to an adsorption step using a tyrosine-immobilized carrier to recover antibody.

A third embodiment of the present invention resides in an anti-sulfated tyrosine monoclonal antibody specific for sulfated tyrosine which is capable of binding to sulfated tyrosine as a free molecule or present as a residue in a peptide chain, but not to unsulfated tyrosine, either as a free molecule or as a residue in a peptide chain.

A fourth embodiment of the present invention provides a hybridoma which is capable of producing the above-described anti-sulfated tyrosine monoclonal antibody specific for sulfated tyrosine.

A fifth embodiment of the present invention provides a process for the production of the above-described anti-sulfated tyrosine monoclonal antibody specific for sulfated tyrosine which comprises culturing the above-described hybridoma and subsequently recovering the monoclonal antibody from the resulting culture mixture.

The anti-sulfated tyrosine antibody specific for sulfated tyrosine according to the present invention has such a reaction specificity that it is capable of binding to sulfated tyrosine in the free state or present in a peptide chain but not to unsulfated tyrosine. As a result of this, the amount of sulfated tyrosine can be measured quantitatively in a simple manner and within a short period of time. In addition, the hybridoma of the present invention is capable of producing anti-sulfated tyrosine monoclonal antibody specific for sulfated tyrosine having this reaction specificity.

Such antibodies specific for sulfated tyrosine can be used for specific measurement of sulfated tyrosine (free or in peptide). Determining the amount of sulfated tyrosine in body fluid may provide new diagnostic significance for various diseases.

These and other objects and advantages of the present invention will be made apparent as the description hereinafter progresses.

DETAILED DESCRIPTION OF THE INVENTION

Figure 1:
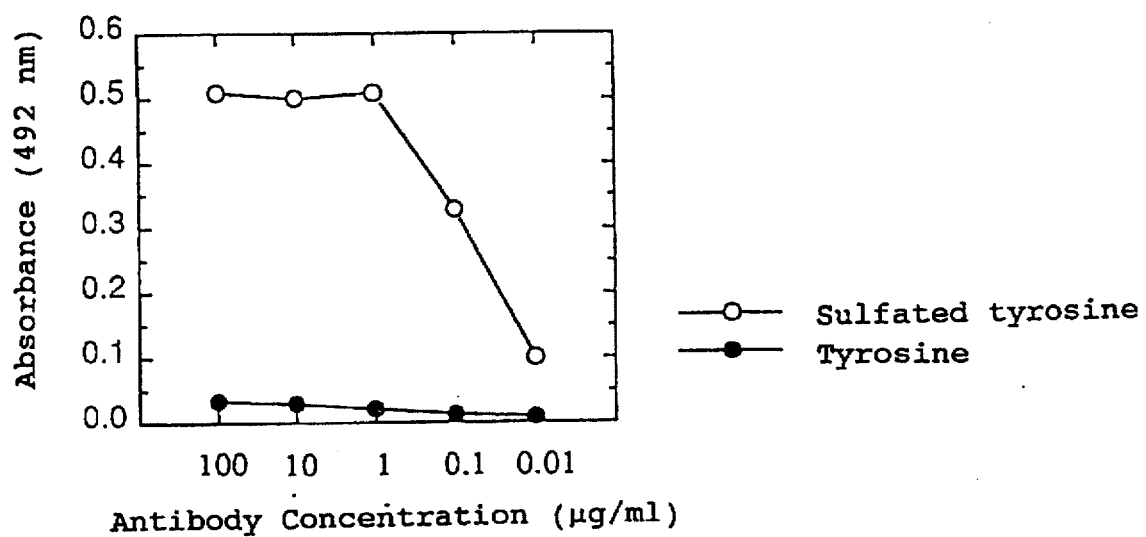
FIG. 1 is a graph showing cross-reactivity of the anti-sulfated tyrosine antibody specific for sulfated tyrosine according to the present invention.

The antibody of the present invention may either be polyclonal or monoclonal, but preferably is monoclonal antibody. It may be any class or subclass of antibody such as IgG, IgM or the like, but preferably is an IgG antibody.

The antibody of the present invention has the following reaction specificities.

(1) It binds to sulfated tyrosine either in the free state or present in a peptide chain through an antigen-antibody reaction.

(2) It substantially does not bind to unsulfated tyrosine in the free state or present in a peptide chain, as shown in FIG. 1.

(3) Its physico-chemical properties except binding specificity, such as molecular weight and the like, are similar to the properties of ordinary antibodies which are already reported for instance in *Medical Immunology* (Third Edition, Igaku Shoin, Japan, 1990). That is, it has a molecular weight of about 130,000 to 210,000, an optimum pH range of from 6 to 9, a stable pH range of from 3 to 11 and an optimum temperature range of from 0° to 40° C.

A polyclonal antibody having these characteristics may be obtained in the following manner.

In general, an antibody can be obtained from a serum sample withdrawn from an animal immunized with an antigen. An anti-sulfated tyrosine antibody can be prepared from a serum sample from an animal immunized with sulfated tyrosine as an antigen. The antibody prepared by the above method, however, may bind not only to sulfated tyrosine but also to unsulfated tyrosine. The present inventor prepared antibodies specific for sulfated tyrosine by employing the sequential chromatography system which was comprises of affinity chromatographies with sulfated and unsulfated tyrosine as a ligand.

This unique method enabled the preparation of the antibody specific for sulfated tyrosine.

Firstly, an appropriate mammal such as a rabbit, a sheep, a goat, a mouse, a rat, a horse or the like is immunized against an appropriate antigen such as a compound obtained by binding sulfated tyrosine as a hapten to a carrier protein such as keyhole limpet hemocyanin (hereinafter referred to as "KLH"), bovine serum albumin (hereinafter referred to as "BSA") or the like by means of the carbodiimide technique or the like, or a protein (fibrinogen, fibronectin or the like) whose tyrosine residues in the peptide chain are sulfated. In this instance, an immunopotentiator such as Freund's complete adjuvant (hereinafter referred to as "FCA") can be effectively used. Next, booster is effected using the same antigen 1 to 8 weeks, preferably 2 to 4 weeks, after the immunization. In this case, an immunopotentiator such as Freund's incomplete adjuvant (hereinafter referred to as "FIA") can be effectively used. Thereafter, final immunization is carried out using sulfated tyrosine. One to 14 days, preferably 3 to 7 days, after the final immunization, a serum sample is collected from the immunized animal. The serum sample thus obtained is passed into a column packed with a carrier (for example, SEPHAROSE which is an agarose-based beaded matrix manufactured by Pharmacia) to which sulfated tyrosine has been immobilized, the adsorbed portion of the sample is eluted using an appropriate eluting solution and then the resulting eluate is passed into a column packed with a carrier (SEPHAROSE, for example) to which tyrosine has been immobilized to remove antibodies that bind not only to sulfated tyrosine but also to unsulfated tyrosine. In this way, an antibody which binds in a specific manner only to sulfated tyrosine is obtained.

A monoclonal antibody having specific binding ability for sulfated tyrosine may be obtained in the following manner.

Firstly, a hybridoma is prepared which can produce a monoclonal antibody capable of binding to sulfated tyrosine in the free state or present in a peptide chain but not to unsulfated tyrosine in the free state or present in a peptide chain. For this purpose, for example, mice are immunized against the same antigen used for the preparation of polyclonal antibody as described above and, after final immunization, the spleens are excised from the immunized mice. Thereafter, myeloma cells and the thus obtained spleen cells are subjected to cell fusion in accordance with a conventionally used method as disclosed for instance in *Monoclonal Antibody* (Kodan-sha Scientific, 1983). As a result, a hybridoma which is capable of producing the anti-sulfated tyrosine antibody specific for sulfated tyrosine is selected out and obtained.

Selection of such an antibody producing hybridoma may be effected using, for example, the following method.

In general, a monoclonal antibody can be obtained by creation and cultivation of a hybridoma, which is created by cell fusion of immunized animal spleen cells and myeloma cells. Thus, an anti-sulfated tyrosine monoclonal antibody can be prepared. The monoclonal antibody prepared by the above method, however, may bind not only to sulfated tyrosine but to unsulfated tyrosine. The present inventor prepared monoclonal antibodies specific for sulfated tyrosine by employing the sequential immunoassay system which was comprised of immunoassays with sulfated and unsulfated tyrosine as an immobilized antigen.

This unique method enabled the preparation of the monoclonal antibodies specific for sulfated tyrosine.

Firstly, sulfated tyrosine is linked to a carrier protein which is different from the one used for the immunization of mice against sulfated tyrosine. The thus linked antigen is fixed on a 96-well microtiter plate. After adding culture supernatants of hybridoma samples to the wells, a hybridoma capable of producing a monoclonal antibody which binds to sulfated tyrosine is selected by the unique sequential combination of two immunoassays in order to choose hybridomas producing monoclonal antibodies specific for sulfated tyrosine. Supernatants of the thus selected hybridoma candidates are added to a 96-well microtiter plate which has been fixed with an antigen prepared by linking tyrosine to a carrier protein that is different from the one used for the immunization of mice against tyrosine. Thereafter, a hybridoma which does not react with tyrosine is selected using enzyme immunoassay, radioimmunoassay or the like. The thus selected hybridoma can be cloned by means of limiting dilution analysis or the like.

A hybridoma capable of producing the anti-sulfated tyrosine monoclonal antibody specific for sulfated tyrosine obtained as described hereinbefore was produced and designated "MSY-2". Hybridoma MSY-2 was deposited on Oct. 30, 1991, in Fermentation Research Institute, Agency of Industrial Science and Technology, Ministry of International Trade and Industry and received accession number FERM BP-3640.

No antibody which binds to sulfated tyrosine but not to unsulfated tyrosine has been reported. The present inventor first obtained such antibodies by means of unique screening technique.

Production of the anti-sulfated tyrosine monoclonal antibody specific for sulfated tyrosine may be achieved, for example, by culturing the thus cloned hybridoma capable of producing the anti-sulfated tyrosine monoclonal antibody specific for sulfated tyrosine using flask culture, hollow fiber culture, an agitator-equipped culture vessel or the like, and then isolating and purifying the antibody of interest from the resulting culture supernatant by ammonium sulfate fractionation, ion exchange chromatography, protein A SEPHAROSE chromatography and the like.

The following examples are given to further illustrate the present invention. It is to be understood, however, that these examples are for purpose of illustration only and are not to be construed as limiting the present invention. Unless otherwise indicated herein, all parts, ratios and the like are by weight.

REFERENCE EXAMPLE 1

A 20 mg portion of bovine fibrinogen (produced by Nacalai Tesque) was dissolved in 4 ml of 50 mM ammonium carbonate solution, and the solution was mixed with bovine thrombin (produced by Sigma) and incubated at 37° C. for 3 hours. The resulting reaction product was passed through a column packed with CM SEPHAROSE (produced by Pharmacia) which has been equilibrated at pH 6.0, thereby removing unsulfated peptides. In this way, 6 mg of fibrinogen peptide B (hereinafter referred to as "FPB") was obtained for use as an antigen.

REFERENCE EXAMPLE 2

A 20 mg portion of sulfated tyrosine and 10 mg of KLH (produced by Sigma) were dissolved in 1.2 ml of distilled water, and the pH of the solution was adjusted to 7. With stirring at room temperature (about 20°–30° C.), to the thus prepared solution was added 1 ml of an aqueous solution containing 0.6 g of 1-ethyl-3-(3-dimethylaminopropyl)-carbodiimide hydrochloride. After 72 hours of reaction at 4° C., the resulting reaction mixture was dialyzed and then freeze-dried to obtain 24 mg of a conjugated product of sulfated tyrosine and KLH.

In the same manner, 25 mg of a conjugated product (sulfated tyrosine-BSA) was prepared from 20 mg of sulfated tyrosine and 12 mg of BSA.

Also in the same manner, 24 mg of a conjugated product (tyrosine-BSA) was prepared from 20 mg of tyrosine and 12 mg of BSA. These products were used as antigens for immunoassay and enzyme immunoassay.

EXAMPLE 1

A 1 mg portion of FPB prepared as described in Reference Example 1 above was dissolved in 1 ml of phosphate-buffered physiological saline (hereinafter referred to as "PBS"), the resulting solution was mixed with the same volume of FCA (produced by Nacalai Tesque), and the thus prepared emulsion was administered to a rabbit by subcutaneous injection. Three weeks after the immunization, booster was effected in the same manner using an emulsion prepared by mixing the same amount of FPB with FIA (produced by Nacalai Tesque). Three weeks later, final immunization was carried out using FPB alone. Blood samples were collected 5 days after the final immunization to obtain 49 ml of serum preparation.

The serum preparation was subjected to 50% saturation ammonium sulfate fractionation. The resulting precipitate was dialyzed against 10 mM phosphate buffer (pH 7.3), adsorbed onto diethylaminoethyl (DEAE) SEPHAROSE (produced by Pharmacia) which had been equilibrated with the same buffer in advance, and then eluted with a sodium chloride density gradient to obtain 23 mg of purified product. The thus obtained purified product was adsorbed onto a column packed with a sulfated tyrosine-immobilized SEPHAROSE (produced by Pharmacia) and then eluted with 0.2M glycine-HCl buffer. The resulting antibody fraction was dialyzed against PBS and then passed through a column packed with a tyrosine-immobilized SEPHAROSE (produced by Pharmacia) to remove tyrosine-binding antibody components. Thereafter, the fraction passing through the column was concentrated with ultrafiltration to obtain 15 mg of rabbit anti-sulfated tyrosine antibody specific for sulfated tyrosine. When checked, the thus obtained antibody showed all of the above-described reaction specificities.

EXAMPLE 2

A 1 mg portion of the sulfated tyrosine-KLH bound product prepared as described in Reference Example 2 above was dissolved in 1 ml of PBS, the resulting solution was mixed with the same volume of FCA (produced by Nacalai Tesque), and the thus prepared emulsion was administered to two mice (BALB/c, purchased from Clea Japan Inc.) by intraperitoneal administration. Three weeks after the immunization, booster was effected in the same manner using an emulsion prepared by mixing the same amount of the sulfated tyrosine-KLH bonded product with FIA (produced by Nacalai Tesque). Three weeks later, final immunization was carried out using sulfated tyrosine alone. Three days after the final immunization, the spleens were excised from the immunized mice to prepare spleen cells which were subsequently suspended in RPMI 1640 medium (produced by Gibco) and mixed with previously cultured myeloma P3•U1 cells (ATCC No. CRL-1597; available from Dianippon Pharmaceutical Co., Ltd.) ($4 \times 10^7$) to effect cell fusion using 50% polyethylene glycol (PEG) 4000 (produced by Sigma).

The thus fused cells were cultured for 2 weeks using HAT selective medium to select hybridoma cells which were subsequently subjected to screening using enzyme immunoassay to isolate a hybridoma capable of producing anti-sulfated tyrosine antibody specific for sulfated tyrosine. That is, supernatants of the thus selected hybridoma candidates were added to a 96-well microtiter plate which has been fixed in advance with the sulfated tyrosine-BSA bound product prepared as described in Reference Example 2. After washing, peroxidase-conjugated goat anti-mouse IgG antibody was added to the microplate and allowed to stand for several hours. Thereafter, the microplate was washed and a substrate solution was added to the washed plate to compare the colors developed in the wells, thereby screening for a hybridoma whose supernatant fluid showed a darker color than the control. The thus screened hybridoma was cloned using limiting dilution analysis.

A hybridoma thus cloned was designated "MSY-2" and was deposited in Fermentation Research Institute, Agency of Industrial Science and Technology, Ministry of International Trade and Industry as described above and has received accession number FERM BP-3640.

A 600 ml portion of GIT medium (produced by Wako Pure Chemical Industries) was inoculated with $6 \times 10^8$ cells of the thus obtained hybridoma MSY-2 (FERM BP-3640), and the cells were cultured at 37° C. for 4 days in the presence of 5% carbon dioxide. After completion of the culturing and removing the cells by centrifugation, the pH of the resulting culture supernatant was adjusted to 9.0 with a sodium hydroxide solution and passed through a column packed with protein A SEPHAROSE. The column was then washed with Tris-HCl buffer (pH 8.6), and the material retained by the column was eluted with glycine-HCl buffer (pH 2.3). Thereafter, the eluted fractions were pooled and dialyzed against PBS to obtain 1.1 mg of an anti-sulfated tyrosine monoclonal antibody specific for sulfated tyrosine (MSYA-2).

Reaction specificity of the thus obtained anti-sulfated tyrosine monoclonal antibody specific for sulfated tyrosine, MSYA-2, was examined by enzyme immunoassay using microtiter plates to which the sulfated tyrosine-BSA or tyrosine-BSA prepared in Reference Example 2 had been fixed. More specifically, a 0.1 mg/ml solution of antibody MSYA-2 was decimally diluted to $10^5$ and added to each plate, followed by 2 hours of allowing the mixture to stand at room temperature. After washing, peroxidase-conjugated goat anti-mouse IgG antibody was added to each plate and the mixture was allowed to stand for 1 hour. Thereafter, the plate was washed and a substrate (ortho-phenylenediamine) was added to the washed plate to measure the activity of the antibody. The results obtained are shown in FIG. 1 in which the absorbance (429 nm) is plotted as the ordinate and the antibody concentration (µg/ml) as the abscissa. As is evident from the results shown in FIG. 1, the antibody of the present invention reacts with sulfated tyrosine even at a concentration of 0.01 µg/ml but hardly with tyrosine showing almost no color development even at an increased tyrosine concentration of 10 µg/ml.

While the invention has been described in detail and with reference to specific embodiments thereof, it will be apparent to one skilled in the art that various changes and modifications can be made therein without departing from the spirit and scope thereof.

What is claimed is:

1. Antibody MSY-2 having accession number FERM BP 3640 which specifically binds sulfated tyrosine as a free molecule or present in a peptide and does not bind to unsulfated tyrosine.

2. A hybridoma which is capable of producing the monoclonal antibody of claim 1.

* * * * *